(12) United States Patent
Fine

(10) Patent No.: US 10,539,570 B2
(45) Date of Patent: Jan. 21, 2020

(54) DIAGNOSTIC TESTING FOR IMMUNOLOGIC FOOD SENSITIVITY

(71) Applicant: Kenneth Davin Fine, Dallas, TX (US)

(72) Inventor: Kenneth Davin Fine, Dallas, TX (US)

( * ) Notice: Subject to any disclaimer, the term of this patent is extended or adjusted under 35 U.S.C. 154(b) by 0 days.

(21) Appl. No.: 16/011,236

(22) Filed: Jun. 18, 2018

(65) Prior Publication Data
US 2018/0299466 A1    Oct. 18, 2018

Related U.S. Application Data

(63) Continuation of application No. 15/098,365, filed on Apr. 14, 2016.

(60) Provisional application No. 62/149,136, filed on Apr. 17, 2015.

(51) Int. Cl.
| *G01N 33/53* | (2006.01) |
|---|---|
| *G01N 33/68* | (2006.01) |
| *G01N 21/78* | (2006.01) |
| *A61B 10/00* | (2006.01) |
| *B01L 3/00* | (2006.01) |
| *G01N 21/75* | (2006.01) |
| *G01N 21/77* | (2006.01) |

(52) U.S. Cl.
CPC ..... *G01N 33/6854* (2013.01); *A61B 10/0038* (2013.01); *B01L 3/5023* (2013.01); *G01N 21/78* (2013.01); *G01N 33/6893* (2013.01); *B01L 2300/0636* (2013.01); *B01L 2300/0825* (2013.01); *G01N 2021/752* (2013.01); *G01N 2021/757* (2013.01); *G01N 2021/7759* (2013.01); *G01N 2800/06* (2013.01); *G01N 2800/24* (2013.01)

(58) Field of Classification Search
None
See application file for complete search history.

(56) References Cited

U.S. PATENT DOCUMENTS

| 5,451,504 A * | 9/1995 | Fitzpatrick | G01N 33/558 435/7.2 |
|---|---|---|---|
| 5,753,787 A * | 5/1998 | Hawdon | C07K 14/4354 435/252.3 |
| 8,450,074 B2 * | 5/2013 | Dodds | G01N 33/564 435/7.1 |
| 2007/0207554 A1 * | 9/2007 | Lin | A61B 10/0045 436/514 |
| 2007/0275475 A1 * | 11/2007 | Liang | B01L 3/502 436/165 |
| 2008/0112847 A1 * | 5/2008 | Chen | G01N 21/03 422/400 |
| 2009/0305303 A1 * | 12/2009 | Duvanel | G01N 33/558 435/7.2 |
| 2013/0184188 A1 * | 7/2013 | Ewart | G01N 33/492 506/39 |

* cited by examiner

*Primary Examiner* — Gary Counts
(74) *Attorney, Agent, or Firm* — Ferguson Braswell Fraser Kubasta PC; Elizabeth Philip Dahm; Kelly J. Kubasta

(57) ABSTRACT

In various implementations, a noninvasive, food sensitivity test may be utilized to identify one or more food sensitivities. A fecal sample may be obtained. The food sensitivity test may be performed on the obtained fecal sample. One or more food sensitivities may be identified based on the food sensitivity test.

20 Claims, 6 Drawing Sheets

DIAGNOSTIC TESTING FOR IMMUNOLOGIC FOOD SENSITIVITY

CROSS-REFERENCE TO RELATED APPLICATION

This application is a continuation of U.S. patent application Ser. No. 15/098,365, entitled "DIAGNOSTIC TESTING FOR IMMUNOLOGIC FOOD SENSITIVITY" and filed on Apr. 14, 2016 and now abandoned, which claims the benefit of U.S. Provisional Patent Application No. 62/149,136, entitled "DIAGNOSTIC TESTING FOR IMMUNOLOGIC FOOD SENSITIVITY" and filed on Apr. 17, 2015, both of which are hereby incorporated by reference for all purposes.

TECHNICAL FIELD

The present invention relates to food sensitivity testing in patients.

BACKGROUND

Currently, chronic immunological food sensitivities (e.g., to be distinguished from acute allergy) and/or intolerance in people may be difficult and/or expensive to identify. Many food products are processed and/or genetically engineered to include portions of other types foods that may not be expected in a product. For example, corn chips may include wheat gluten. Thus identifying food sensitivities from an elimination diet may be difficult. In addition, needless elimination diets (e.g., when food sensitivities are not present) may cause unintended calorie restriction and/or nutritional deficiencies. Scratch tests and blood tests may be expensive, cause discomfort, and/or prevent some people from pursuing testing. Furthermore, since children and/or some adults (e.g., adults with impaired abilities) may not be able to accurately tell others about their experiences, food sensitivities may go unnoticed and/or may be difficult to ascertain and continue to cause immunological reactions. Undiagnosed food sensitivities may cause prolonged immunological reactions, which contribute to the poor health of an individual, and may cause or complicate management of other diseases and/or disorders.

SUMMARY

In various implementations, a noninvasive, food sensitivity test may be utilized to identify one or more food sensitivities and/or facilitate identification of diseases and/or disorders. The food sensitivity testing system may include a food sensitivity test, fecal sample collection set (e.g., tools to transfer feces, specimen container, fecal sample collection device, etc.), and/or other components. A fecal sample from a patient may be obtained. The food sensitivity test may be performed on the obtained fecal sample. One or more food sensitivities may be identified based on the performance of the food sensitivity test on the fecal sample. In some implementations, one or more diseases or disorders associated with the identified food sensitivity may be identified.

In various implementations, a diagnostic test kit may identify food sensitivity in humans. The kit may include a diagnostic test to identify the presence of a first set of food sensitivities in a human. The diagnostic test may include a substrate and a test region. The test region may include antibody binding agent(s) coupled to the substrate. The antibody binding agent(s) may couple with first antibodies, associated with one or more of the foods sensitivities in the first set of food sensitivities, when the first antibodies are present in a fecal sample obtained from the human. The diagnostic test may contact the fecal sample of the human to allow identification of the presence of the first set of food sensitivities. The first antibodies, if present in the fecal sample, may be transferred to the test region of the diagnostic test by the contact.

Implementations may include one or more of the following features. The diagnostic test may be a stick test. The stick test may include a first end and an opposing second end. The first end of the stick test may include a handle to allow a user to hold the stick test without contacting the fecal sample. The second end of the stick test may contact the fecal test to allow transfer of one or more of the first antibodies, if present in the fecal sample, to the test region of the diagnostic test. The diagnostic test may include an absorbent region to transfer a testing portion of a fecal sample from the fecal sample to the test region of the diagnostic test. The absorbent region may contact the fecal sample and absorbs fluid from the fecal sample to transfer to the test region. The fluid from the fecal sample may include at least a portion of the antibodies present in the fecal sample. The diagnostic test may include one or more flags to indicate coupling of one or more first antibodies in a fecal sample with one or more of the antibody binding agents of the diagnostic test. The flag(s) may provide a visual indication that at least one of the first set of food sensitivities is present in the human associated with the fecal sample. The diagnostic test may allow fluid from the fecal sample to flow between two or more regions of the diagnostic test. The antibody binding agent(s) may include an IgA conjugate associated with an IgA antibody associated with one or more food sensitivities in the set of food sensitivities, wherein the IgA conjugate binds to the IgA antibody when the IgA antibody is proximate the IgA conjugate. The testing region of the diagnostic test includes flag(s) coupled to one or more of the antibody binding agents such that flag(s) are altered when an antibody from a fecal sample couples with an antibody binding agent. Altering one or more of the flags produces a visually identifiable change. The testing region may include a plurality of different antibody binding agents associated with different food sensitivities. In some implementations, the diagnostic test may be integrated with a specimen container. The specimen container may allow a testing portion of the fecal sample to be disposed in the specimen container to allow identification of the first set of food sensitivities. The diagnostic test may be positioned in the specimen container to allow contact with the testing portion of the fecal sample.

In various implementations, a diagnostic test kit may identify food sensitivity in humans. The kit may include a fecal sample collection tool and one or more diagnostic tests integrated in the fecal sample collection tool. The diagnostic tests may identify the presence of a first set of food sensitivities in a human. The diagnostic test(s) may include a substrate and a test region. The test region may include one or more antibody binding agents coupled to the substrate. At least one of the antibody binding agents may couple with one or more first antibodies associated with the first set of food sensitivities when one or more of the first antibodies is present in the fecal sample obtained from the human. The fecal sample collection tool may allow one or more of the diagnostic tests to contact the fecal sample to allow identification of the presence of the first set of food sensitivities. The first antibodies, if present in the fecal sample, may be transferred to the test region of the diagnostic test by the contact.

Implementations may include one or more of the following features. One or more of the food sensitivity tests may be positioned in the fecal sample collection tool such that the food sensitivity test(s) contacts the fecal sample. One or more of the food sensitivity tests may be positioned on the fecal sample collection tool such that a testing portion of the fecal sample is moved to contact the food sensitivity test(s) and allow identification of the first set of food sensitivities. The fecal sample collection tool may include opening(s) to allow at least a portion of fluid from a fecal sample to drain from the fecal sample collection tool. The fecal sample collection tool may allow a hydrating agent and/or a solution including flags to be applied to the fecal sample in the fecal sample collection tool. The diagnostic test(s) may include flag(s) to indicate coupling of one or more first antibodies in the fecal sample with one or more of the antibody binding agents in the diagnostic test(s). The flag(s) may provide a visual indication that at least one of the first set of food sensitivities is present in the human associated with the fecal sample. The fecal sample collection tool may include a removable stop. The stop may close an opening in the fecal sample collection tool, and when the stop is removed at least one of fluid and/or the fecal sample may be drained from the fecal sample collection tool via the opening. The diagnostic test may include a plurality of antibody binding agents associated with a set of foods. At least one of the antibody binding agents may include an IgA conjugate associated with an IgA antibody associated with one or more food sensitivities in the set of food sensitivities. The IgA conjugate may bind to the IgA antibody when the IgA antibody is proximate the IgA conjugate. The testing region may include one or more flags coupled to one or more of the antibody binding agents such that when an antibody couples with an antibody binding agent the flag is altered. The diagnostic test(s) may provide a visually identifiable change to identify the presence of the first set of food sensitivities in the fecal sample.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which.

Like reference symbols in the various drawings indicate like elements.

DETAILED DESCRIPTION

Figure 1A:
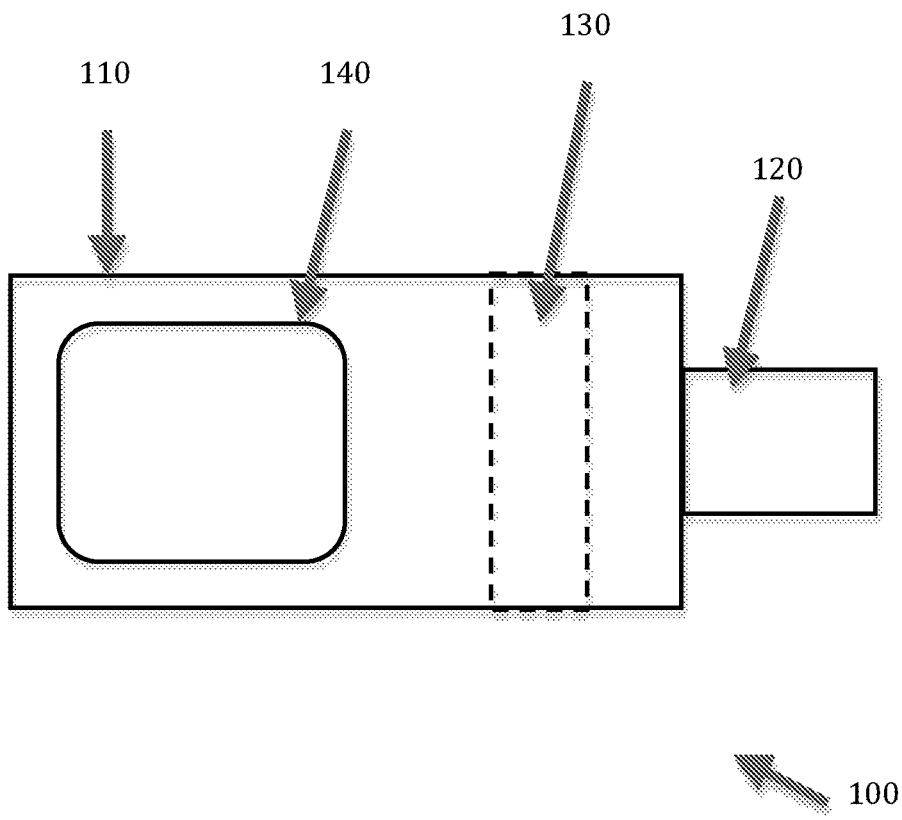
FIG. 1A illustrates an implementation of an example food sensitivity test.

In various implementations, a food sensitivity testing system may be provided. Food sensitivities may include immunological reactions in a person in response to ingesting, consuming, injecting, and/or contacting foods or portions thereof. For example, when a person experiences sensitivity to an immunogenic food, the food may act as an antigen and the person's body may produce antibodies specific to the antigen (e.g., the food). The produced antibodies may include Immunoglobulin A (IgA). When a person consumes a food that acts as an antigen in the body, the food specific IgA in the body may bind to the antigen (e.g., the food) and cause an immunological reaction and/or symptom (e.g., inflammation, diarrhea, nausea, etc.). Since IgA is produced in mucosal linings and present in the gastrointestinal tract, feces from the person may include IgA.

In various implementations, the food sensitivity test may be noninvasive since the food sensitivity test is performed on a fecal sample. In patients, such as children and impaired adults (e.g., intellectual disabilities, dementia, Alzheimer's, etc.), invasive tests, such as blood tests and skin tests may cause patient fear and/or discomfort. In addition, blood collection from children is difficult due to patient fear and small blood vessel sizes. Thus, patient fear and/or discomfort may be reduced (e.g., when compared with invasive testing) using the food sensitivity test. In some patients, blood collection is impractical due to underlying health issues (e.g., poor clotting due to health and/or medications).

When food sensitivities are determined based on fecal samples, the levels of Immunoglobin A (IgA) present in the fecal sample are utilized to identify food sensitivities. In some implementations, measurement of IgA may provide a more accurate reflection of food sensitivities related to the mucus secretions and/or gastrointestinal system (e.g., than IgE) since IgA is produced in mucosal linings and is present in the gastrointestinal tract. In some implementations, sampling blood for IgA, IgG, or IgE antibodies may accompany and/or complement the fecal IgA testing.

The identification of food sensitivities may be utilized to diagnose symptoms, such as chronic gastrointestinal symptomatology (including but not limited to vomiting, diarrhea, constipation, foul/malodorous flatulence and/or stools, and abdominal bloating), behavioral problems, or chronic immune/auto-immune sequelae; and/or specific disorders and diseases, including gluten-sensitive enteropathy, Crohn's Disease, and/or irritable bowel syndrome; reduce immunological sensitivities (e.g., by eliminating the identified food); and/or other appropriate purposes. In some implementations, the food sensitivities identified by testing fecal samples and/or diagnoses of patients may be further tested using conventional methods, such as ELISA blood serum testing, skin prick testing, and/or endoscopy.

In various implementations, the food sensitivity test may include a testing region on a substrate. The substrate may include a plate (e.g., nanoparticle plate, microfluidic array, sensor on chip, etc.), a test strip, a stick such as the food sensitivity test stick described in FIG. 1, a container (e.g., a cup and/or bowl), and/or other appropriate testing substrate. In some implementations, the fecal sample may be collected directly in and/or on the substrate. The fecal sample may be collected and transferred to the substrate of a food sensitivity test, in some implementations.

The testing region may include antibody binding agent. The antibody binding agent may include a compound with a receptor capable of selectively binding (e.g., the antibody binding agent may not bind with one or more other antibodies) with a predetermined antibody. For example, the antibody binding agent may include an antibody conjugate, such as an IgA conjugate (e.g., corn IgA conjugate, wheat IgA conjugate, etc). The antibody binding agent may be disposed on a substrate of the food sensitivity test. The antibody binding agent may be applied to the testing region prior to and/or before the fecal sample or portions thereof are disposed on the testing region. The antibody binding agents may be bound (e.g., immobilized and/or coupled via methods similar to ELISA) on the testing region, in some implementations. For example, antibody binding agents, such as antigens, may be bound on a substrate of the testing region. For example, when a food sensitivity test is adapted to identify corn sensitivities, the antibody binding agent may be adapted to selectively bind with corn IgA (e.g., IgA produced in response to an immunological food sensitivity reaction to corn) while being inhibited from coupling with other types of IgA, such as wheat IgA, egg IgA, corn IgE, etc. By utilizing antibody binding agents that selectively couple with predetermined antibodies (e.g., rather than coupling with predetermined antibodies and other antibodies), false indications of food sensitivities may be reduced (e.g., when compared a test that utilizes nonselectively coupling antibody binding agents). In some implementations, the antibody binding agent may be coupled by passive adsorption to a test region of the substrate. For example, a solution of the antibody binding agent (e.g., in an alkaline buffer solution) may be contacted with substrate(s) and allowed to incubate. Then the solution may be removed or washed off such that antibody binding agents remain coupled to portion(s) of the substrate.

The coupling between the antibody binding agent and the predetermined antibody may be chemical coupling and/or affinities between regions of the antibody binding agent and the predetermined antibody. For example, an antibody binding agent may include an antigen for a predetermined antibody. When the antibody is in the presence of the antibody binding agent (e.g., antigen), the antibody and the antibody binding agent (e.g., antigen) may couple. The antibody binding agent (e.g., IgA conjugate) may include a receptor capable of coupling with a predetermined portion of a predetermined antibody. For example, an antibody binding agent may include an antigen (e.g., corn IgA conjugate and/or other appropriate antigens) for a predetermined antibody (e.g., corn IgA, antigliadin IgA, antitissue transglutaminase IgA antibody; and/or other appropriate antibodies). The predetermined portion of the antibody may not be present on one or more other antibodies, and thus binding of the antibody binding agents with one or more other antibodies may be inhibited.

During use, the fecal sample or portions (e.g., testing portion) there of may be provided to (e.g., contacted with, pass over, etc.) the testing region of the food sensitivity test. The predetermined antibodies (e.g., that the test is seeking to identify), if present in the fecal sample, may bind with the antibody binding agents in the testing region. The use of flags with the food sensitivity test may facilitate identification of the antibody-antibody binding agent coupling.

The food sensitivity test may include a flag to provide notifications to a user. For example, the food sensitivity test may include a flag that identifies predetermined couplings (e.g., between the antibody binding agent and the antibody, between a flag binding agent and the flag, etc.). The flags may be disposed in a flag region of the food sensitivity test, coupled to antibody binding agents, and/or otherwise provided with the food sensitivity test.

The flag may include, for example, color markers, radioopaque markers, magnetic markers, fluorescent label (e.g., via a fluorophore), and/or any other appropriate flag (e.g., flags that provide audio, visual, and/or tactile indications). Utilizing flags may facilitate identification of predetermined couplings, such as between antibody binding agents and predetermined antibodies, and thus facilitate identification of food sensitivities. Utilizing flags may ease use by users, in some implementations. For example, a user may be able to view the food sensitivity test and determine the results based on visualization of the flags or lack of flags. In some implementations, when the antibody binding agent and antibody bind, the flag may change colors (e.g., not visible to visible; white to red; red to blue; fluoresce; and/or combinations thereof). The user may then compare the changed color to an instruction set to determine if a food sensitivity exists based on the results (e.g., instruction set may include a color chart, color intensity chart, etc. that associates visual cues with results such as a specific set of food sensitivities).

In some implementations, the fecal sample may be processed prior to contacting the testing region. In some implementations, processing the fecal sample may include coupling a flag to predetermined antibodies, if present, in the fecal sample. For example, a solution comprising the flags may be allowed to wash over at least a portion of the fecal sample. In some implementations, at least a portion of the fecal sample may be allowed to flow through a region of the food sensitivity test that includes flags. If predetermined antibodies are present in the fecal sample, one or more of the flags may be coupled to the predetermined antibodies. In some implementations, a hydrating solution (e.g., water, saline, and/or other appropriate solutions) may be added to the fecal sample to allow testing. For example, if a fecal sample is dry, water may be added to the fecal sample. In some implementations, the fecal sample may be mixed or otherwise agitated (e.g., to produce an approximately homogenous fecal sample). In some implementations, an undiluted fecal sample may be provided to the testing region of the food sensitivity test.

In some implementations, the test region of the food sensitivity test may include a control. The control may provide an indication that the food sensitivity test is capable of identifying predetermined antibodies. For example, the control may include flag binding agents. The flag binding agents may be capable of selectively coupling with the flag present in the food sensitivity test and may not be capable of binding with other flags. When a flag contacts the control of the test region, the flag may bind with the flag binding agent and provide an indication, such as a color change.

The user may utilize the results of the food sensitivity test to provide an initial and/or dispositive indication of a food sensitivity associated with the set of antibodies for which the test was selected. In some implementations, the user may follow up the results with additional home testing, clinical testing, and/or laboratory testing of fecal samples, blood samples, and/or other testing (e.g., examination of intestines). After food sensitivity is identified using the food sensitivity test, disorders and/or diseases associated with the food sensitivity may be identified based at least partially on the one or more food sensitivities identified using the food sensitivity test. For example, if gluten sensitivity is identified by the food sensitivity test, Crohn's disease may be identified in the person based on the results of the food sensitivity test and/or other medical information about the person (e.g., weight loss, no cancer detected).

In some implementations, a first food sensitivity test may be utilized with a fecal sample or portion thereof (e.g., testing portion) from an individual to determine whether a set of food sensitivities is present. One or more subsequent food sensitivity tests may be performed based on the results of the first food sensitivity test. For example, if the results of the first food sensitivity test indicate (e.g., via color alteration) a food sensitivity but not which food sensitivity in the set of food sensitivities, then one or more second food sensitivity tests may be performed to determined which of the food sensitivities in the set is present in the individual being tested (e.g., if a set for the first test includes corn, wheat and dairy, the second test may test for corn and wheat and a third test may test for dairy; if a set for a first set includes wheat, dairy and eggs, the subsequent tests may test for each item individually). In some implementations, if the results of the first food sensitivity test does not indicate (e.g., no color change) that any of the food sensitivities in the set of food sensitivities are present in the individual, further testing may not be performed and/or subsequent testing on different sets of food sensitivities may be performed.

In some implementations, the food sensitivity testing system may include a home kit. The home kit may include a fecal sample container, food sensitivity test, and/or instructions.

In various implementations, the food sensitivity testing system may include a food sensitivity test, fecal sample kit, and/or other components. The food sensitivity test may be selected to facilitate use in a home setting. For example, the food sensitivity test may be single use, self-contained (e.g., washing with specialty reagents may not be performed), easy to use, and/or cost-effective. The food sensitivity test may allow fecal sample testing without processing and/or with minimal processing (e.g., stirring and/or diluting). The food sensitivity test may allow testing of undiluted fecal samples, in some implementations.

Figure 1B:
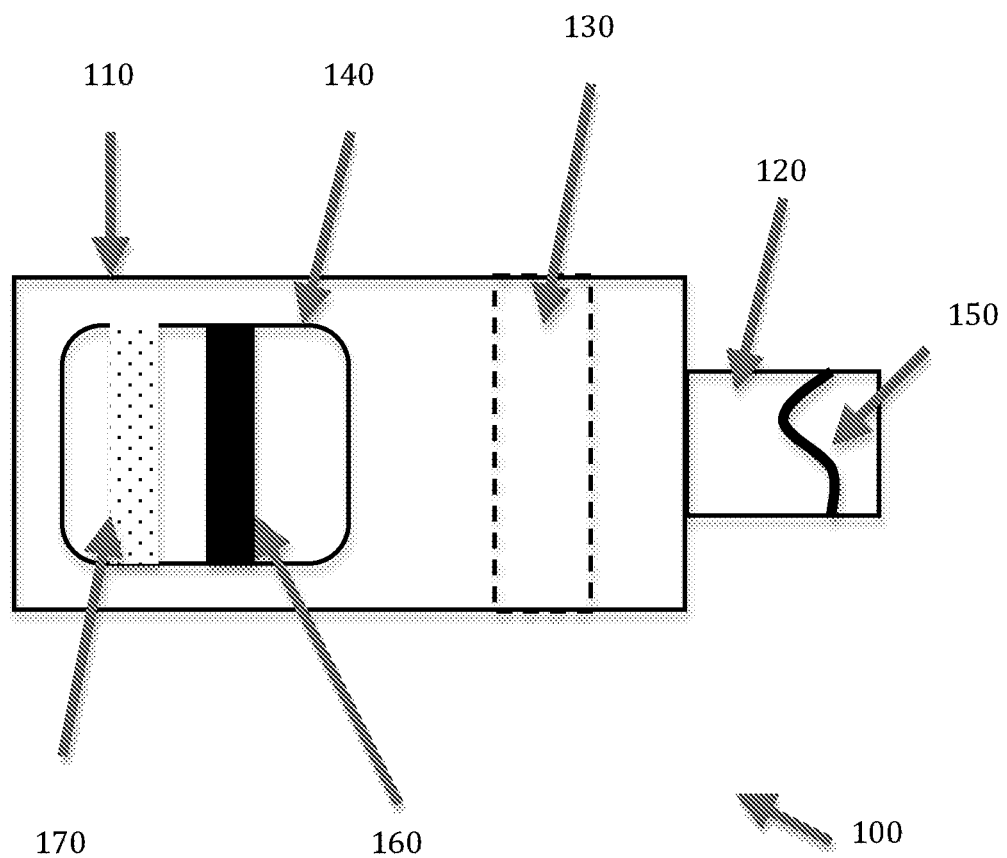
FIG. 1B illustrates an implementation of the example food sensitivity test illustrated in FIG. 1A, during use.

FIG. 1A illustrates an implementation of an example of a food sensitivity test 100. FIG. 1B illustrates the food sensitivity test 100 during use. The food sensitivity test 100 may allow rapid, easy to read results. Using the food sensitivity test may be easier for users, since the stick may not include steps such as washing plates with specialized reagents, complex ordering of steps, applying flags, and/or specialized visualization of flags (e.g., via microscope, via radioimaging, and/or via other visualization methods). In addition, fecal sample testing may be performed without additional processing and/or lengthy additional processing steps, in some implementations.

The food sensitivity test may include a first end and a second opposing end. At least a portion of the food sensitivity test 100 (e.g., proximate the first end) may be disposed in a housing 110. The housing 110 may allow a user to hold the food sensitivity test 100 without touching one or more regions of the food sensitivity test stick (e.g., the absorbent region 120) and/or the fecal sample. The second end of the food sensitivity test may be contact a fecal sample to allow testing of the fecal sample. For example, the second end may be positioned in (e.g., stuck in, pushed in, etc.) the fecal sample to allow testing. In some implementations, the second end of the food sensitivity test may be positioned in a wet portion of the fecal sample to encourage fluid (e.g., containing IgA from the fecal sample) flow from the fecal sample into the food sensitivity test.

The food sensitivity test 100 may include an absorbent region 120, a flag region 130, and a test region 140. The regions of the food sensitivity test 100 may be on a substrate, such as a continuous substrate. In some implementations, the regions may not be on a continuous substrate and the food sensitivity test may allow fluid flow between one or more regions. The substrate may include absorbent pad(s), woven fiber(s) (e.g., synthetic and/or natural fibers), microfluidic channel(s) and/or paper(s), in some implementations.

The absorbent region may draw fluid into the food sensitivity test from the fecal sample. For example, the absorbent region may draw fluid from a fecal sample at least partially into one or more other regions of the food sensitivity test stick. The absorbent region may draw at least a portion of the fluid by absorption, capillary action, pressure differentials, pumping (e.g., pipette and bulb), and/or any other appropriate fluid transport mechanism. In some implementations, water may be added to the fecal sample to facilitate drawing at least a portion of the fecal sample into the food sensitivity test stick. In some implementations, the fecal sample may include enough water to allow at least a portion of the fecal sample (e.g., water and/or antibodies in the fecal sample) to be drawn into the food sensitivity test stick.

The absorbent region of the food sensitivity test stick may be placed in contact with the fecal sample (e.g., by pushing the absorbent pad into the fecal sample, by placing the absorbent pad in the supernatant water collected from a centrifuged fecal sample, etc.). As illustrated in FIG. 1B, the absorbent region 120 may transport at least a portion of one or more fluids 250 from the fecal sample through the absorbent region and to another region, such as the flag region 130, of the food sensitivity test 100.

In the flag region, the testing portion of the fecal sample (e.g., a portion of the fecal sample) may flow at least partially through the flag region. In the flag region, flag may selectively bind to predetermined antibodies, if these predetermined antibodies are present in the testing portion of the fecal sample. In some implementations, flags in the flag region of the food sensitivity test may be released into the testing portion of the fecal sample as it passes through the flag region and to the test region. The flags may bind to the antibody binding agents and/or antibodies.

In some implementations, the food sensitivity test stick may not include a flag region. For example, the fecal sample may be contacted with flags (e.g., wash or otherwise apply a solution including flags onto the fecal sample) prior to placing the food sensitivity test stick in contact with the fecal sample.

The food sensitivity test stick may include a test region. The test region may include antibody binding agents. The antibody binding agents may include any appropriate compound (e.g., enzyme, reagent, antigen) that is capable of selectively binding with a predetermined antibody. In some implementations, the antibody binding agent for an IgA antibody may include the associated antigen. For example, the antibody binding agent for the IgA antibody associated with corn sensitivity may include corn antigen (e.g., corn or portions thereof, such as proteins of the corn, as the antigen). If IgA antibody associated with corn is present in a fecal sample, it will bind with corn antigen. The corn antigen may not bind with other IgA present in the fecal sample, such as IgA associated with dairy. Thus, a sensitivity to corn may be identified through the selective coupling of the antibody with an antibody binding agent. By utilizing antibody binding agents that selectively couple with predetermined antibodies (e.g., rather than coupling with predetermined antibodies and other antibodies), false indications of food sensitivities may be reduced (e.g., when compared a test that utilizes nonselectively coupling antibody binding agents).

In the testing region, the flag may be visible or otherwise apparent (e.g., tactile signal) when the antibody, the antibody binding agent and the flag are coupled. Thus, the presence of a predetermined antibody may be identified based on the visualization or other identification of the flag. As illustrated in FIG. 1B, when the flag is coupled to the control (e.g., including flag binding agents), a visible signal 260 may be produced in the test region 140. When the antibody is coupled to the antibody binding agent, the flag may produce, for example, a visible signal 270 in the test region 140. In some implementations, the testing region may include an immunoassay strip.

In some implementations, the flag region and the test region of the food sensitivity test stick may be combined. In some implementations, the flags may be coupled to the control and/or antibody binding agents. For example, flags may be coupled to the antibody binding agents and/or with the control region of the food sensitivity test stick. In some implementations, the flags may be disposed in the testing region and as fluid (e.g., from the fecal sample) travels at least partially through the testing region, the fluid may contact flag(s) and/or antibody binding agents. In some implementations, the flags may be coupled to the antibody binding agent and the flags may provide an indication when the antibody binding agent is coupled to a predetermined antibody. In some implementations, the control may provide an indication that the food sensitivity test is capable of identifying food sensitivities by providing an indication that fluid is present in the testing region (e.g., rather than identifying the presence of flags).

The food sensitivity test allows food sensitivities to be identified based on signals provided by the food sensitivity test. For example, a user may select a set of food sensitivities for which to test. Since the antibodies for different foods may be different, a test is associated with a set of food sensitivities based on which antibody binding agents are present in the testing region. The user may then select the appropriate food sensitivity test based on the type(s) of food to be tested. For example, since the antibodies associated with wheat sensitivity may be different to the antibodies associated with egg sensitivity, the antibody binding agents on the food sensitivity test for each a set of foods may be different to allow the selective coupling between the predetermined antibody and antibody binding agent. The user (e.g., while holding the housing of the food sensitivity test) may allow the absorbing region of the food sensitivity test to contact a fecal sample (e.g., feces or portions thereof) from a user. The fecal sample may include fluids (e.g., water, urea, and/or mucus) and the fluids may include antibodies, if present in the fecal sample. At least a portion of the fluid from the fecal sample may be drawn into the absorbent region of the food sensitivity test (e.g., via capillary action, absorption, drawn to materials in the absorbent region). At least a portion of the fluid in the absorbent region may be drawn (e.g., via capillary action, absorption, pressure differential, and/or or otherwise drawn) between the various regions of the food sensitivity test.

At least a portion of the fluid in the absorbent region may be allowed to flow from the absorbent region to the flag region. In the flag region, if antibodies, associated with the food sensitivities for which the test is selected, are present in the fluid from the fecal sample, the antibodies may couple with flag(s). For example, the flag(s) may be embedded in the material of the flag region and as the fluid from the fecal sample passes through the flag region, the flags may be released and selectively bind with one or more specific antibodies, if present. The specific antibodies may be the antibodies associated with the food sensitivities for which the food sensitivity test is selected. The fluid, possibly including the specific antibodies bound to flags, may then pass to the testing region. In the testing region, antibody binding agents may be present (e.g., coupled to the testing region, washed over the testing region). The fluid may pass proximate the antibody binding agents. If specific antibodies are present in the fluid, the antibody binding agents and the specific antibodies may couple. When the antibody binding agent and the specific antibody couple, the flag may provide an indication (e.g., visible color) of the presence of the coupled antibody. In some implementations, the food sensitivity test may include a control. The control may, for example, include flag binding agents. As the fluid from the fecal sample passes through the testing region, the fluid may pass proximate the control. The flag binding agents may couple with flags (e.g., coupled flags and/or uncoupled flags) in the fluid. In some implementations, the antibody binding agents and/or the control may be coupled to the testing region in a specific pattern to facilitate identification (e.g., lines, circles, etc.). In some implementations, an intensity of the indication provided by the flags (e.g., intensity of color) may indicate a level (e.g., an approximate relative amount, such as a ratio, and/or an approximate absolute amount) of antibodies present in the fecal sample. Thus, based on the indication provided by the flags in the testing region, a user may be able to identify if the test was executed appropriately (e.g., when the control provides an indication), whether specific antibodies are present, and/or a level of antibodies.

In some implementations, the food sensitivity test may be used to determine whether a person has a set of food sensitivities. A set of food sensitivities may include one or more food sensitivities. For example, a test may be utilized to determine if a person has food sensitivities to a set of grains. A test may be utilized to determine if a person has food sensitivities to one or more food substances (e.g., grain, dairy, and/or eggs, common allergens), in some implementations. Additional testing (e.g., additional food sensitivity tests and/or other tests) may be performed if the food sensitivity test indicates sensitivity to one or more of the food sensitivities associated with the food sensitivity test.

In some implementations, a food sensitivity test that is associated with a plurality of food sensitivities may or may not distinguish between the indications provided for each of the food sensitivities. For example, a food sensitivity test may be associated with corn sensitivity, wheat sensitivity, and supplement sensitivity. The flag region may include one or more flags that selectively bind with one or more of the antibodies associated with each of these sensitivities. The flag coupled to a first antibody, such as corn antibody (e.g., the antibody associated with a corn sensitivity), may provide the same indication (e.g., blue and/or fluoresce) as the flag or a different flag in the flag region coupled with one or more of the other antibodies associated with the test (e.g., wheat antibody and/or supplement A antibody). Thus, the indication provided by the flag in the testing region may identify one or more food sensitivity (e.g., by the indication provided by the flags coupling with antibodies and antibody binding agents) and may not distinguish between the different food sensitivities.

In some implementations, when a food sensitivity test is associated with testing a plurality of food sensitivities, the food sensitivity test may allow distinguishing between the food sensitivities identified. For example, each food sensitivity may be associated with a flag that provides a specific indication (e.g., a specific color). In some implementations, the food sensitivity may be associated with a particular part of the testing region. For example, the antibody binding agents may be coupled to the testing region in lines, and so when an indication is provided along a line of the testing region, the food sensitivity type may be determined based on the location of the line.

In some implementations, a food sensitivity tests may be performed as a routine diagnostic test. Since undiagnosed food sensitivities can harm a user, and since a noninvasive test may be performed, the use of the food sensitivity test may be performed without waiting for symptoms to present in a patient. For example, newborns may be screened for lactose and/or soy intolerance. Elderly residents at hospices may be screened for food intolerance to common food preparations and/or food supplements (e.g., dietary supplements such as nutritional shakes).

In some implementations, a user who suspects food sensitivities can utilize home food sensitivity tests to diagnose and/or preliminarily identify food sensitivities. For example, food sensitivity testing such as blood tests and/or skin prick tests can be expensive when performed in a clinical setting. The food sensitivity test may allow food testing to be performed cost-effectively, easily (e.g., since fecal samples may not need to be transported to a laboratory or clinic), and/or while maintaining privacy (e.g., since a test can be self-administered).

A user may select a food sensitivity test based on the set of foods to be tested. A food sensitivity test may allow testing of a set (e.g., one or more) of predetermined group of foods (e.g., same types of foods, such as grains; set of common allergens, such as dairy, eggs, and wheat; etc.). The food sensitivity test may include antigen binding agents and flags that are capable of coupling with the antibodies produced by the set of foods associated with the food sensitivity test. For example, a user may select a first food sensitivity test for a first set of foods and a second food sensitivity test for a second set of foods. Thus, a user may select which sets of food sensitivities to test for and which sets of food sensitivities to skip. In addition, the user may perform additional testing based on the results of a first set of food sensitivity tests. For example, if a food sensitivity is identified with a first food sensitivity test, then additional testing (e.g., via additional food sensitivity tests) may be performed to further identify which specific foods or portions thereof (e.g., proteins) cause the food sensitivity. In some implementations, when a first food sensitivity test does not identify food sensitivity to the set of foods associated with the first food sensitivity test, the user may perform one or more additional food sensitivity tests associated with one or more different sets of foods.

In some implementations, the food sensitivity test may be utilized to determine efficacy of diet changes. For example, a set of food sensitivities for an individual may be identified (e.g., based on the food sensitivity test result) and the individual's diet may be altered to reduce and/or eliminate one or more of the foods identified. Subsequent food sensitivity test(s) may be performed to determine whether overall sensitivity has been reduced. In some implementations, one or more foods may be added back into the diet based on the subsequent testing. For example, if an individual has a "leaky gut" based on inflammation, the individual may have increased overall sensitivity and an initial test may show positive reactivity (e.g., positive for food sensitivity) for multiple foods. After elimination of one or more of these foods (e.g., in the set associated with positive food sensitivity), the individual's overall inflammation and/or overall sensitivity may be decreased. The decrease in inflammation and/or sensitivity (e.g., when compared with the initial test), may identify the foods for which the individual has food sensitivity and which foods that were previously indentified as in the set of foods to which the individual is sensitive were misidentified based on the overall inflammation. For example, an initial test may identify that an individual, who has a "leaky gut," has food sensitivity to wheat, cow's milk, and soy. After elimination of wheat, cow's milk, and soy from the diet of individual for a first predetermined period, subsequent food sensitivity test(s) may be performed on fecal samples from the individual. The subsequent test results may indicate that wheat sensitivity is present but sensitivity to cow's milk and soy is not present. The reduction in the sensitivity to cow's milk and soy may be based on a reduction in overall inflammation and/or sensitivity, and the diet of individual may be adjusted to all reintroduction of one or more of these items. By allowing subsequent testing, the individual's quality of life may be improved (e.g., since inflammation may be decreased and/or symptoms of food sensitivities may be decreased) and/or unnecessary diet and/or calorie restriction may be inhibited.

In some implementations, a fecal sample may be obtained from a user via a provided specimen container. In some implementations, a user may collect a fecal sample. For example, the food sensitivity test and/or kit may include a specimen container (e.g., jar, tray). The user may use a collection tool, such as a tongue blade, to transfer a portion of feces collected from a person to the specimen container.

In some implementations, the fecal sample may be further processed prior to testing the fecal sample. The fecal sample may be concentrated. For example, the fecal sample may be placed in a centrifuge (e.g., to be rotated at speeds of approximately 13,500 rpm to approximately 20,000 rpm) and the supernatant fluid may be tested. In some implementations, the fecal sample may be freeze dried (e.g., lyophilized). Water may be added to the freeze dried fecal sample prior to testing the fecal sample. In some implementations, freeze drying the fecal sample may facilitate testing of different types of fecal matter (e.g., watery fecal matter).

In some implementations, the fecal sample may not be placed into a specimen container prior to testing the fecal sample with the food sensitivity test. For example, a user may insert a stick based food sensitivity test directly into feces from a user. In some implementations, water may be added to the feces and/or the feces may be mixed with water (e.g., with the collection tool and/or with the food sensitivity test, such as mixing with the absorbent end of the food sensitivity test) prior to inserting the food sensitivity test into the feces.

Figure 3:
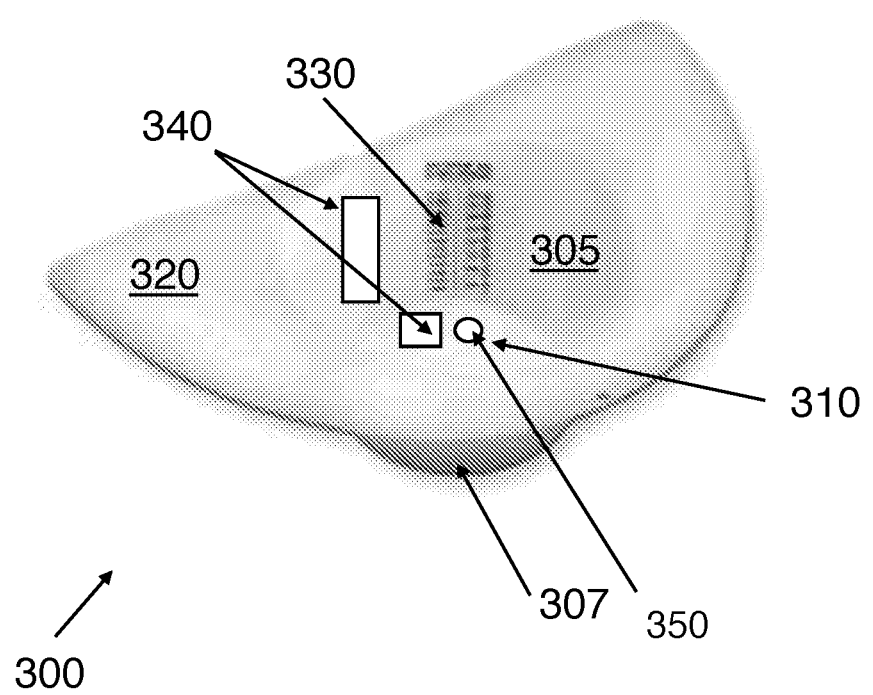
FIG. 3 illustrates an implementation of an example integrated fecal collection tool.

In some implementations, the fecal collection tool may include an integrated food sensitivity test. For example, the fecal collection tool may include a hat like shape or other appropriate shape. FIG. 3 illustrates an implementation of an example fecal collection tool 300 with an integrated food sensitivity test. The fecal collection tool may include an inner surface and an outer surface. As illustrated, the fecal collection tool 300 includes a collection portion 310 and a rim 320. The collection portion 310 may be shaped and sized to hold a fecal sample. The rim 320 may facilitate fecal collection. As illustrated, the rim 320 may extend (e.g., radially) from the collection portion 310; and during use, one or more portions of the rim 320 may contact a toilet (e.g., toilet rim and/or seat). In some implementations, the rim may be collapsible (e.g., the rim may include radial flanges that can be collapsed, the rim may include flanges that collapse in, the rim may include flanges that fold inwards to form a cover, etc.). As illustrated the fecal collection portion 310 may have walls and a bottom surface. The collection portion 310 may include measuring tools 330, such as markings to indicate volume or any other appropriate measuring tool. The measuring tools may be disposed on an inner surface of the fecal collection tool 300.

The food sensitivity test 340 may be integrated with the collection portion 310. As illustrated, the food sensitivity test 340 may be positioned on a wall of the collection portion and/or on a bottom of a collection portion. In some implementations, multiple food sensitivity tests may be provided on a fecal collection tool. The food sensitivity test(s) 340 may be positioned on an inner surface 305 of the fecal collection tool, as illustrated. As illustrated, the opening 350 may be disposed proximate a bottom of the fecal collection tool. In some implementations, a removable stop (e.g., a stop that can be removed and/or reinserted) (not shown) may be disposed in the opening 350 to inhibit fluids and/or solids from flowing through the fecal collection tool.

Figure 4A:
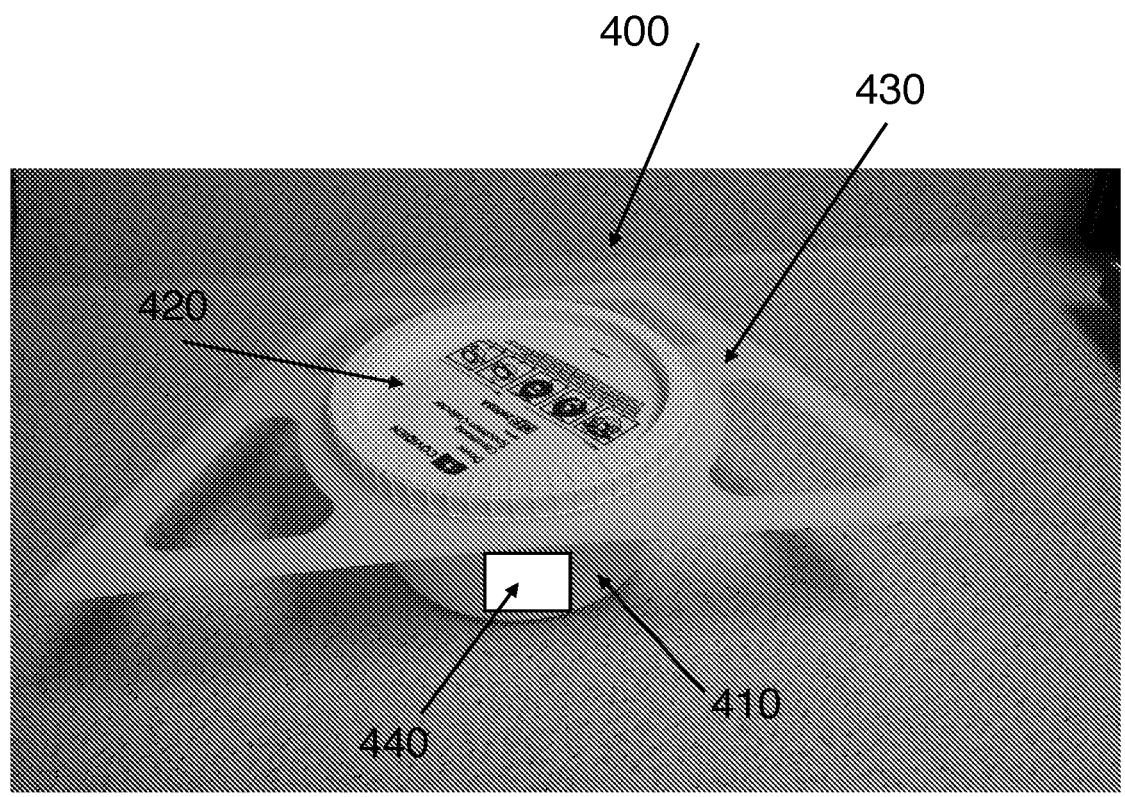
FIG. 4A illustrates an implementation of an example integrated fecal collection tool.
Figure 4B:
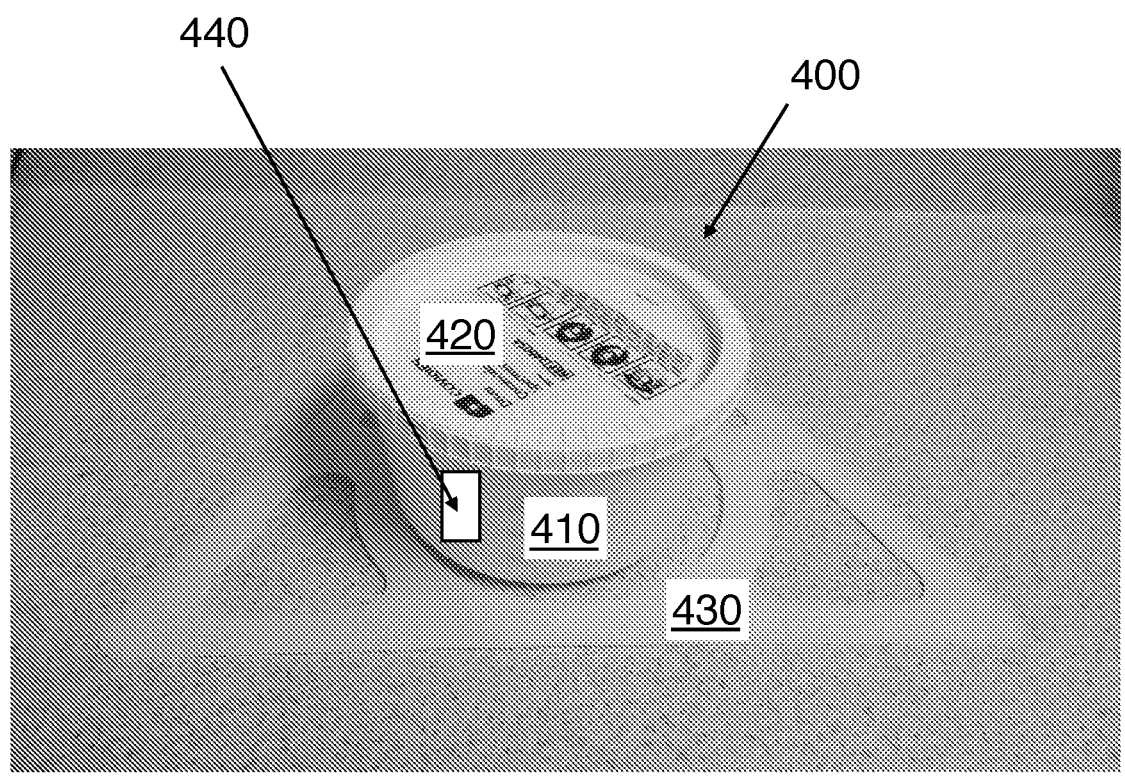
FIG. 4B illustrates an implementation of the example integrated fecal collection tool illustrated in FIG. 4A in which the collar has been removed.

In some implementations, the fecal collection tool may have a shape that allows at least a portion of the container to contact the edges of a toilet, rest in place under the toilet seat, and/or at least partially be secured by toilet such that during use, the fecal collection tool may remain positioned (e.g., not fall completely into toilet bowl to make removal of the fecal collection tool more difficult). FIG. 4A illustrates an implementation of an example fecal collection tool 400 and FIG. 4B illustrates the fecal collection tool 400 in which the collar has been removed. As illustrated, fecal collection tool 400 includes a collection portion 410, cover 420, and a collar 430. The cover 420 may allow the collection portion to be closed (e.g., for transport, for disposal, etc.). The collar 430 may be removable. As illustrated, the collar may include an opening in which the collection portion 410 can be disposed (e.g., without falling through the opening). The collar 430 may include a rim, and the rim or portions thereof may contact on a portion of a toilet (e.g., rest on or between toilet rim and/or seat) during use. By utilizing a removable rim, the fecal collection tool 400 may facilitate use. For example, the collar may be attached during fecal sample collection and removed to view test results, send the fecal sample to a laboratory for further testing, etc. The fecal collection tool may include a food sensitivity test (not shown) on an inner surface of the collection portion. During use, at least a portion of the fecal sample may contact or be allowed to contact (e.g., a user may move a portion of the fecal sample to contact) the food sensitivity test. As illustrated, the testing portion 440 and/or results (not shown) of the food sensitivity test may be visible from an outer surface of the fecal collection tool. For example, the collection portion may be formed of a transparent and/or translucent material that allows viewing of the food sensitivity test from an outer surface. In some implementations, the food sensitivity test may be disposed in an opening of the fecal collection tool and the food sensitivity test may be viewable from the outer surface. In some implementations, the absorbent region of the food sensitivity test may be disposed on an inner surface of the fecal collection tool, to allow contact between the absorbent region and the fecal sample or portions thereof. The testing portion or portions thereof may be disposed on an outer surface of the fecal collection tool to allow viewing of the testing portion and/or results.

The fecal collection tool may include pan with an opening to allow liquids (e.g., urine) to drain from the pan, while the pan is capable of holding thicker or solid fecal samples. The opening may allow the fecal sample to be drained from the fecal collection tool after testing (e.g., for disposal and/or into another container for storage and/or further testing). The opening may be disposed in a bottom portion and/or side portion(s) of the fecal collection tool. The fecal collection tool may include one or more opening(s) that may have any appropriate position, size (e.g., large enough to allow a fluid to drain and/or not large enough to allow the fecal sample to fall through the opening if a stop is not utilized) and/or shape (e.g., circular, rectangular, etc.). For example, the fecal collection tool may include a plurality of slits that act as openings to allow at least a portion of the fluid to drain from the fecal collection tool. In some implementations, the openings may include an opening with a removable stop.

In some implementations, the fecal collection tool may have opening and a stop. For example, the stop may not block the opening during sample collection (e.g., such that urine may pass); the stop may then be allowed to block the opening to allow testing and/or fecal sample processing. In some implementations, the stop may be allowed to block the opening during fecal sample collection and the stop may be removed at a later point (e.g., to drain at least a portion of urine in the fecal collection tool, to drain at least a portion of a flag solution applied to the fecal sample in the fecal collection tool, to drain at least a portion of hydrating solution applied to the fecal sample, and/or to remove the fecal sample from the fecal collection tool). The fecal collection tool may be capable of coupling or otherwise being disposed in a toilet for ease of use. The fecal collection tool may include a testing region disposed in an area of the pan in which fecal samples may be collected. For example, one or more walls of the pan of a fecal collection tool may be slanted to promote contact of the fecal sample with the testing region of the food sensitivity test. The fecal sample may be allowed to remain in contact with a fecal sample collected in the fecal collection tool for a first period of time. As the fecal sample is in contact with the testing region, antibodies, if present in the fecal sample, may contact with flags and/or antibody testing regions. In some implementations, water or another hydrating agent may be provided in the pan to at least partially hydrate the fecal sample and/or facilitate fluids from the fecal sample flowing proximate and/or in the testing region. After the first period of time the fecal sample may be moved from the area proximate the testing region, removed from the pan and/or the pan may be rinsed (e.g., with water). The user may then be able to view the testing region and/or indications provided by flags. Food sensitivities may be identified from the indications, as previously described. The fecal collection tool may include a handle to allow a user to hold the fecal collection tool in place while not contacting feces.

In some implementations, the specimen container and the food sensitivity test may be integrated. For example, a specimen container may include a testing region. For example, the testing region may be disposed on a wall or bottom of the container. A portion of a fecal sample may be transferred (e.g., from a diaper) to the specimen container. The fecal sample may contact the testing region and/or water may be added to allow the fecal sample to hydrate and/or contact the testing region. As the fecal sample is in contact with the testing region, antibodies, if present in the fecal sample, may contact with flags and/or antibody testing regions to provide indications. The indications may indicate the presence or absence of food sensitivities. In some implementations, after the first period of time the fecal sample may be moved from the area proximate the testing region, removed from the pan and/or the pan may be rinsed (e.g., with water). The user may then be able to view the testing region and/or indications provided by flags. Food sensitivities may be identified from the indications, as previously described.

In some implementations, the food sensitivity test may allow testing of a plurality of antibodies associated with a single food (e.g., corn, dairy, eggs, a specific supplement). Since a food, food A, may include more than part that may trigger immunological reactions, an person may produce more than one type of antibody in response to contact (e.g., touching, consuming, etc.) with food A. For example, a species of fish may have several different types of proteins within the fish. A person that contacts the fish, by for example eating the fish, may produce more than one type of antibody in response, if the person has an immunological reaction to the fish. In some people, a person may have a reaction to a first protein in the fish but not have a reaction to a second protein in the fish. An immunological reaction to each of these proteins may produce different antibodies. Thus, if an immunological test includes an antibody binding agent that selectively couples to the antibody produced in response to the first protein and not the antibody produced in response to the second protein, the immunological test may produce a false negative (e.g., the person has a food sensitivity but it is not identified by the test). Thus, a food sensitivity test includes antibody binding agents for more than one protein associated with a food to decrease the rate of false negatives (e.g., when compared with a test that only includes a single type of antibody binding agent). The flags may produce indications for each of the antibody—antibody binding agent bindings that are similar or different based on the type of protein associated with the antibody. For example, a home kit may include several types of proteins but not distinguish between sensitivities to the several proteins (e.g., since a user may not care which protein the person has a sensitivity but has concerns about a particular food). In some implementations, a testing kit (e.g., a laboratory kit) may include a food sensitivity test that distinguishes between indications associated with different proteins (e.g., to provide a more detailed analysis, to identify other sources of the protein that may cause immunological reactions, etc.).

In some implementations, the food sensitivity testing system may include utilizing successively specific food sensitivity tests to reduce the number of tests to perform, to facilitate usability by the user, to reduce costs, to provide specificity requested from a user, etc. For example, one or more first food sensitivity test may be used to identify whether a person has food sensitivities to a first set of foods. If the results are negative (e.g., no food sensitivity detected), then rather than having to purchase and perform a test for each of the foods individually a single test may provide results. If a result is positive (e.g., a food sensitivity detected), then additional testing may be performed using second food sensitivity tests. For example, the second food sensitivity tests may identify a smaller second set of food sensitivities than the first set of foods. The second set may be associated with one or more foods. Additional tests, such as third food sensitivity tests may be performed based on the results of the second food sensitivity tests.

Figure 2:
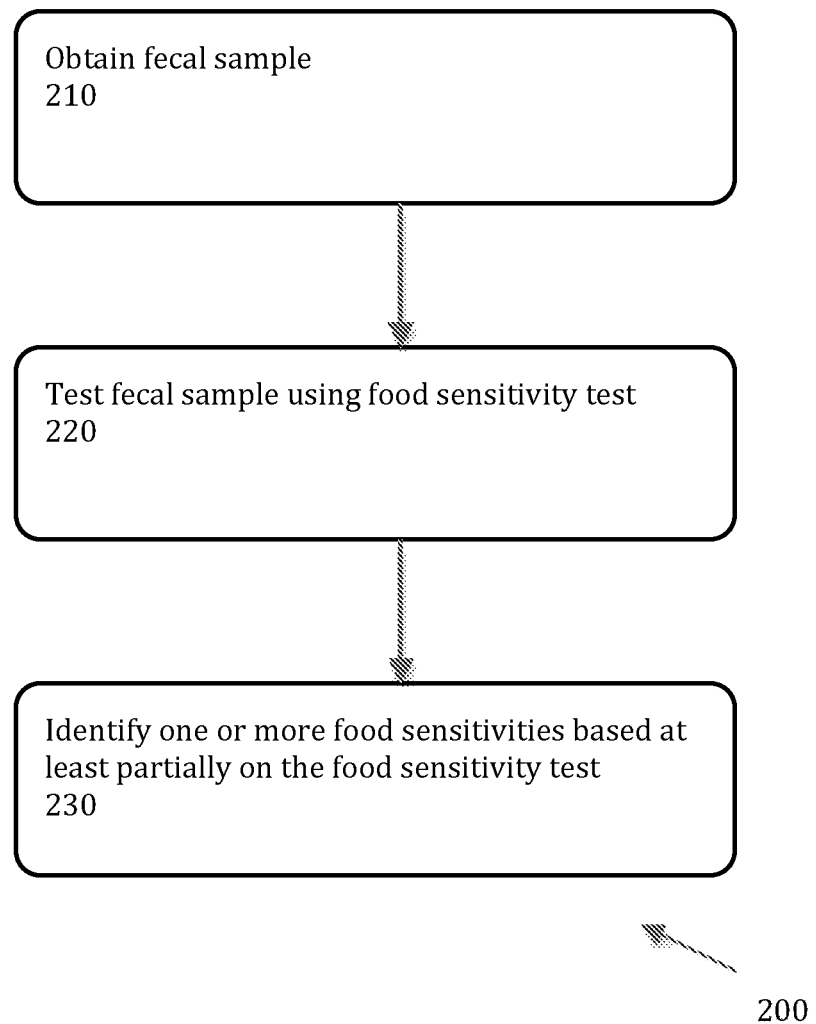
FIG. 2 illustrates an implementation of an example process for testing for food sensitivities.

In various implementations, a food sensitivity test may allow identification of a set of food sensitivities in people. FIG. 2 illustrates an implementation of an example of a process for identifying food sensitivities. A fecal sample may be obtained (operation 210). The fecal sample may be tested using the food sensitivity test (operation 220). During testing of fecal samples with the food sensitivity test, the food sensitivity test may be contacted with a fecal sample. For example, supernatant liquid from a fecal sample may be deposited on the food sensitivity test. In some implementations, the food sensitivity test may be dipped into the fecal sample. The fecal sample may be processed to bind a flag (e.g., color, fluorescence, magnetic flag, and/or other detectable indicators) to a predetermined antibody, if present in the fecal sample. The flag may be activated (e.g., the color may change, the flag may fluoresce, etc.) when the flag is coupled to an antibody binding agent, in some implementations. In some implementations, fluids in at least a portion of the fecal sample may flow through (e.g., through a chamber, through channel(s), etc.) a flag region such that predetermined antibodies, if present in the fecal sample, may contact and couple with the flag. Thus, when the food sensitivity test is contacted with the fecal sample, if antibodies are present in the fecal sample, the antibodies will couple with the antibody binding agents on the substrate of the test and the flag may be activated.

One or more food sensitivities may be identified based at least partially on the food sensitivity test (operation 230). For example, the fecal sample obtained from a person may include food specific IgA, in levels detectable by the food sensitivity test. Activation of the flag(s) in the testing region may provide indicia to facilitate identification of the predetermined antibody in the fecal sample, and thus food sensitivity related the predetermined antibody.

In some implementations, the food sensitivity test may include a test strip. The test strip may include antibody binding agent that when coupled to a predetermined antibody produces an indicia (e.g., color change, fluorescence, etc.).

In some implementations, one or more food sensitivity tests may be performed on the same fecal sample (e.g., the same testing portion and/or another testing portion from the same fecal sample). For example, a food sensitivity test may be associated with a first set of foods (e.g., common allergens, gluten panel, grain panel, additives panel, and/or any other appropriate set that can be performed together). The first food sensitivity test may produce a first result (e.g., food sensitivity to one or more of the first set of food sensitivities). Subsequent food sensitivity test(s) may be performed based on the first results from the first food sensitivity test. For example, if a first food sensitivity test does not distinguish between the food sensitivity in the first set (e.g., a positive or negative reactivity is produced for the overall set), and the first result is positive reactivity then one or more subsequent food sensitivity tests may be performed to specify the identify of the food sensitivity (e.g., the subsequent test may include a portion of the food sensitivities in the first set of food sensitivities associated with the first test). In some implementations, if a first food sensitivity test is negative, then subsequent food sensitivity test(s) may be performed with one or more second sets of food sensitivities (e.g., including at least one different food sensitivity from the first set of food sensitivities). In some implementations, by testing for multiple food sensitivities with one food sensitivity test, costs may be reduced and results may be obtained more quickly (e.g., when compared with running a screening of a plurality of food sensitivities).

In some implementations, a user may purchase a kit of food sensitivity test(s) and select one or more to perform on a fecal sample. In some implementations, a user may purchase a kit with a fecal collection tool integrated with one or more food sensitivity test(s) and one or more separate food sensitivity test(s). The user may determine which, if any separate food sensitivity test(s) to perform based on the results from the food sensitivity test(s) integrated with the fecal collection tool. For example, a user use separate food sensitivity test(s) associated with different sets of food sensitivities and/or subsets of the food sensitivities tested for using the integrated food sensitivity test(s). In some implementations, the separate food sensitivity test(s) may be utilized for confirmatory testing.

In some implementations, the fecal sample may be processed and/or unprocessed prior to allowing the food sensitivity test to identify food sensitivities. For example, the fecal sample may be obtained and an undiluted and/or unconcentrated fecal sample may be utilized with the food sensitivity test. In some implementations, a food sensitivity test may be dipped into an undiluted and unconcentrated fecal sample.

In some implementations, the fecal sample may be concentrated prior to allowing the food sensitivity test to identify food sensitivities. A fecal sample may be obtained and concentrated. For example, the fecal sample may be centrifuged (e.g., at approximately 13,500 rpm-approximately 20,000 rpm or any appropriate velocity). The supernatant liquid from the centrifuged fecal sample may be collected, in some implementations. The food sensitivity test may be performed on the supernatant liquid. For example, the food sensitivity test may be dipped into the supernatant liquid to identify food sensitivities.

In some implementations, the fecal sample may be overly watery (e.g., due to diarrhea). The fecal sample may be concentrated to facilitate identification of food sensitivities. For example, the fecal sample may be freeze dried. The solid freeze dried fecal sample obtained may then be reconstituted with a hydrating agent (e.g., water) to an appropriate moisture content (e.g., to allow appropriate testing using the food sensitivity test). For example, the percentage of dry to wet may be approximately 25 percent to approximately 75 percent and/or any other appropriate ratios. In some implementations, the freeze dried fecal sample may be reconstituted to a similar moisture content of non-diarrhea stool (e.g., less than the moisture content of the original fecal sample).

In some implementations, the fecal sample may be overly dry (e.g., due to constipation and/or moisture loss due to age of fecal sample). The fecal sample may be hydrated to allow moisture to transport the antibodies, if present in the fecal sample, into the food sensitivity test. For example, water or another hydrating agent may be added to the fecal sample. The hydrating agent may be added to the fecal sample to obtain a moisture content in a predetermined range (e.g., approximately 25 percent to approximately 75 percent, a moisture content associated with nonconstipated stool, a moisture content that allows transportation of antibodies present in the fecal sample through the absorbent region of the food sensitivity test and/or any other appropriate moisture content). In some implementations, the fecal collection tool may be used to mix the fecal sample and the water. The hydrated fecal sample may then be utilized with the food sensitivity test. For example, the food sensitivity test may be dipped into the hydrated fecal sample.

Although food sensitivities have been used to describe an immunologic sensitivity to a food, food sensitivity may also refer to an immunologic sensitivity to a particular food substance. For example, food sensitivity may refer to an immunologic sensitivity to a food dye. Food sensitivity may refer to an immunologic sensitivity to a food additive. In some implementations, food sensitivity may refer to an immunologic sensitivity to a vitamin, supplement, nutraceutical, pharmaceutical, and/or other products consumed by a person.

The food sensitivity tests may be for use in a clinical (e.g., in office and/or point of care testing), laboratory, and/or home environment.

In various implementations, diagnosing of food sensitivities using the food sensitivity test has been described. The presence of specific IgA may be used to identify food sensitivities and/or diseases and/or ranges of IgA that indicate food sensitivity, are described in U.S. Pat. No. 6,667,160 to Fine and U.S. Pat. No. 7,604,957 to Fine, which are incorporated by reference to the extent that the patents are not contradictory to the disclosure provided herein.

In various implementations, an agent has been described. An agent may include antibodies, antigens, cells, enzymes, markers, and/or portions thereof.

In various implementations, selective coupling has been described. Selective coupling may include allowing coupling between a first agent and one or more second agent and restricting coupling between the first agent and one or more third agents. The second agents may include a single type of or multiple types of the agent. The third agent may include a single type of agent and/or multiple types of agents.

Although users have been described as a human, a user may be a person or a group of people.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a food" includes a combination of two or more foods and reference to "a test" includes different types and/or combinations of tests.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A system comprising:
a diagnostic test to identify food sensitivity in a human by detecting a presence of a first set of human food sensitivities in the human, wherein the diagnostic test comprises:
a substrate;
an absorbent region adapted to transfer a testing portion of a fecal sample from the fecal sample to a test region of the diagnostic test, wherein the absorbent region contacts the fecal sample and absorbs fluid from the fecal sample to transfer to the test region, and wherein the fluid from the fecal sample comprises at least a portion of the antibodies present in the fecal sample;
the test region, wherein the test region comprises one or more human antibody binding agents coupled to the substrate, wherein at least one of the human antibody binding agents is adapted to couple to one or more first antibodies associated with one or more human food sensitivities in the first set of food sensitivities when one or more of the first antibodies is present in a human fecal sample obtained;

a first end, wherein the first end comprises a handle to allow a user to hold the diagnostic test without contacting the human fecal sample; and a second opposing end, wherein the second opposing end is configured to allow the absorbent region to contact the human fecal sample to allow identification of the presence of the first set of food sensitivities; and wherein one or more of the first antibodies, if present in the fecal sample, is transferred to the test region of the diagnostic test by the contact.

2. The system of claim 1 wherein the diagnostic test further comprises one or more flags adapted to indicate coupling of one or more first antibodies in a fecal sample with one or more of the antibody binding agents of the diagnostic test, and wherein one or more of the flags provides a visual indication that at least one of the first set of food sensitivities is present in the human associated with the fecal sample.

3. The system of claim 1 wherein the testing region comprises one or more flags coupled to one or more of the antibody binding agents such that each flag is altered when an antibody from a fecal sample couples with an antibody binding agent, and wherein altering one or more of the flags produces a visually identifiable change.

4. The system of claim 1 wherein the testing region comprises a plurality of different antibody binding agents associated with a plurality of different food sensitivities.

5. A system to identify human food sensitivity, wherein the system comprises:

a human fecal sample collection tool comprising a collection portion; and one or more diagnostic tests to identify human food sensitivity by detecting a presence of a first set of human food sensitivities, wherein each of the one or more diagnostic tests are integrated with the collection portion of the human fecal sample collection tool such that a human fecal sample collected from a human in the collection portion of the human fecal sample collection tool is capable of contacting at least one of the diagnostic tests, and wherein each of the diagnostic tests comprise:

a substrate; and a test region, wherein the test region comprises one or more human antibody binding agents coupled to the substrate, and wherein at least one of the human antibody binding agents is adapted to couple to one or more first antibodies associated with the first set of food sensitivities when one or more of the first antibodies is present in the human fecal sample;

wherein the human fecal sample collection tool is adapted to allow at least one of the diagnostic tests integrated on the fecal sample collection tool to contact the human fecal sample in the collection portion of the human fecal sample collection tool to allow identification of the presence of the first set of food sensitivities; and wherein one or more of the first antibodies, if present in the fecal sample, is transferred to the test region of at least one of the diagnostic tests by the contact.

6. The system of claim 5 wherein one or more of the diagnostic test is positioned in the fecal sample collection tool such that the diagnostic test contacts the fecal sample during collection of the fecal sample.

7. The system of claim 5 wherein one or more of the diagnostic tests are positioned on the fecal sample collection tool such that a testing portion of the fecal sample is moved by a user to contact one or more of the diagnostic tests and allow identification of the first set of food sensitivities.

8. The system of claim 5 wherein the collection portion of the fecal sample collection tool includes one or more openings to allow at least a portion of fluid from a fecal sample to drain from the fecal sample collection tool.

9. The system of claim 5 wherein the fecal sample collection tool is adapted to allow at least one of a hydrating agent or a solution including flags to be applied to the fecal sample in the fecal sample collection tool.

10. The system of claim 5 wherein at least one of the diagnostic tests comprises one or more flags adapted to indicate coupling of one or more first antibodies in the fecal sample with one or more of the antibody binding agents, and wherein one or more of the flags provides a visual indication that at least one of the first set of food sensitivities is present in the human associated with the fecal sample.

11. The system of claim 5 wherein the collection portion of the fecal sample collection tool comprises a removable stop, and wherein the stop is adapted to close an opening in the collection portion of fecal sample collection tool, and wherein when the stop is removed at least one of fluid and/or the fecal sample may be drained from the fecal sample collection tool via the opening.

12. The system of claim 5 wherein the diagnostic test comprises a plurality of antibody binding agents associated with a set of foods.

13. The system of claim 5 wherein at least one of the antibody binding agents comprises an IgA conjugate associated with an IgA antibody associated with one or more food sensitivities in the set of food sensitivities, wherein the IgA conjugate binds to the IgA antibody when the IgA antibody is proximate the IgA conjugate.

14. The system of claim 5 wherein the testing region comprises one or more flags coupled to one or more of the antibody binding agents such that when an antibody couples with an antibody binding agent the flag is altered.

15. The system of claim 5 wherein each of the diagnostic tests is adapted to provide a visually identifiable change to identify the presence of the first set of food sensitivities in the fecal sample.

16. A method of identifying food sensitivity in a human, the method comprising:

collecting a human fecal sample in a collection portion of a human fecal sample collection tool, wherein the human fecal sample collection tool comprises:

one or more diagnostic tests to identify human food sensitivity by detecting a presence of a first set of human food sensitivities, wherein each of the one or more diagnostic tests are integrated with the collection portion of the human fecal sample collection tool such that a human fecal sample collected from a human in the collection portion of the human fecal sample collection tool is capable of contacting at least one of the diagnostic tests in the collection portion, and wherein each of the diagnostic tests comprises:

a substrate; and a test region, wherein the test region comprises one or more human antibody binding agents coupled to the substrate, wherein at least one of the human antibody binding agents is adapted to couple to one or more first antibodies associated with one or more food sensitivities in the first set of food sensitivities when one or more of the first antibodies is present in a human fecal sample;

allowing at least a portion of the obtained human fecal sample in the collection portion to directly contact at least one of the diagnostic tests integrated in the collection portion to allow identification of the presence of the first set of food sensitivities; and wherein one or more of the first antibodies, if present in the fecal sample, is transferred to the test region of at least one of the diagnostic tests by the contact; and detecting a presence of a first set of food sensitivities in the human based on the results in the test region of the diagnostic test.

17. The system of claim 5 wherein the human fecal sample collection tool further comprises a rim disposed at least partially about the collection portion.

18. The system of claim 5 wherein the human fecal sample collection tool further comprises a removable collar extending from the collection portion.

19. The system of claim 5 wherein one or more of the openings comprise one or more slits in the collection portion of the human fecal sample collection tool, and wherein the one or more slits allow at least a portion of fluid from a fecal sample to drain from the fecal sample collection tool.

20. The system of claim 5 further comprising a cover capable of being disposed over the collection portion to closing the collection portion.

* * * * *